United States Patent [19]
Kilgour et al.

[11] Patent Number: 5,760,116
[45] Date of Patent: Jun. 2, 1998

US005760116A

[54] ELASTOMER GELS CONTAINING VOLATILE, LOW MOLECULAR WEIGHT SILICONES

[75] Inventors: John A. Kilgour, Clifton Park; Virginia Van Valkenburgh Powell, East Nassau, both of N.Y.

[73] Assignee: General Electric Company, Waterford, N.Y.

[21] Appl. No.: 708,436

[22] Filed: Sep. 5, 1996

[51] Int. Cl.$^6$ .............................. C08L 83/05; C08L 83/07

[52] U.S. Cl. .................. 524/268; 524/267; 524/731; 525/478; 528/15; 424/78.03

[58] Field of Search ............................. 524/268, 267, 524/731; 525/478; 528/15; 424/78.03

[56] References Cited

U.S. PATENT DOCUMENTS

| | | |
|---|---|---|
| 4,780,145 | 10/1988 | Mori et al. . |
| 4,970,252 | 11/1990 | Sakuta et al. . |
| 4,983,388 | 1/1991 | Kuwata et al. . |
| 4,987,169 | 1/1991 | Kuwata et al. . |
| 5,236,986 | 8/1993 | Sakuta . |
| 5,403,580 | 4/1995 | Bujanowski et al. . |
| 5,468,477 | 11/1995 | Kumar et al. . |

*Primary Examiner*—Patricia A. Short
*Attorney, Agent, or Firm*—Kenneth S. Wheelock

[57] ABSTRACT

A composition comprising the hydrosilylation addition product of a linear alkenyl functionalized polyorganosiloxane and an $M^HQ$ resin and a low molecular weight silicone when subjected to shearing provides for components in personal care formulations that have improved spreadability and substance.

30 Claims, No Drawings

ELASTOMER GELS CONTAINING VOLATILE, LOW MOLECULAR WEIGHT SILICONES

FIELD OF THE INVENTION

The present invention relates to a silicone composition useful as a thickening agent for low molecular weight volatile silicones. The present invention also relates to a process for rendering silicone comprising gels flowable by the mixing low molecular weight silicones with the gel and processing the mixture.

BACKGROUND OF THE INVENTION

Silicones have many uses in a variety of fields. They have found large commercial application in products as diverse as sealants, silicone rubbers, adhesives and cosmetics. Silicone oils have been found to be particularly desirable components of cosmetic compositions because the materials impart a dry, smooth uniform feel to the cosmetic composition among other benefits such as increasing apparent luster (or shine). The general use of silicones in cosmetic formulations has been complicated somewhat by the facts that while lower molecular weight silicones impart desirable properties to a composition they are volatile and have low viscosity, while the silicones that overcome these disadvantages are undesirably viscous.

Thus when it has been desirable to utilize low viscosity silicone oils in a cosmetic application, thickening agents have been employed to increase the solution viscosity and slow down the evaporative loss of the volatile low molecular weight silicone oil. This procedure while effective has the disadvantage of decreasing the spreadability of the silicone oil and leaves a heavy greasy feel on the skin. The spreadability and dry smooth feel are properties associated with low viscosity silicone that imparts a desirable feel or hand to the composition when it is applied as a cosmetic formulation. Materials that have found application in attempting to retain the desirable properties of low molecular weight silicone oils in cosmetic compositions while reducing evaporative losses due to high volatility have been among others fatty acid esters of dextrin, fatty acid esters of sucrose, trimethylsilyl substituted polyvinyl alcohols, trimethylsilyl substituted poly saccharides, cellulose ethers containing fatty acid esters, and organically modified clay minerals. These materials have the disadvantage that the light feeling and spreadability imparted by the low viscosity silicone oil is changed with the result that the composition no longer possesses those properties that suggested the use of the low viscosity silicone oil in the first place. Another disadvantage of these thickening agents or volatility inhibitors is that a large number of them are water soluble and must be used as a water dispersions or solutions. With hydrophobic silicone oils the introduction of water thus necessitates the use of emulsifiers and compatibilizers, complicating the formulation of the cosmetic and generally lowering the stability of the formulation with respect to separation of the component phases.

Recently, another approach to retaining the properties of low viscosity silicone oils in cosmetic compositions has been advanced where the low viscosity silicone oil is combined with the addition polymerization product between an organohydrogen polysiloxane and an alkenyl functionalized organopolysiloxane (U.S. Pat. No. 4,987,169). The organohydrogen polysiloxane utilized in those formulations comprised $HSiO_{1.5}$ ($T^H$), $RSiO_{1.5}$ (T), RHSiO ($D^H$), $R_2SiO$ (D), $R_2HSiO_{0.5}$ ($M^H$) and $R_3SiO_{0.5}$ (M) groups. The crosslinking hydride compound utilized was thus a compound of the general formula: $M_aM^H_bD_cD^H_dT_eT^H_f$. While the cross-linking compound admits T groups either as hydride or substituted by R the preference in this technology is for linear hydride materials because the addition polymerization proceeds more smoothly. The R groups in the above formulas are typical organic substituents known in the art. Subsequently a low molecular weight silicone oil is added to the cross-linked addition polymerized product and the mixture is treated by applying a shearing force. This material may be used by itself as a cosmetic component or as a thickening agent and has the properties of a grease and can be used in a wide variety of industrial lubrication applications as well as the cosmetic application contemplated. The material prepared in this manner can be regarded as a lightly cross-linked elastomer with a volatile, low molecular weight silicone oil dissolved therein. Because the precursor cross-linking hydride is preferably linear and only moderately branched when T groups are incorporated, the addition polymerized product does not possess a tight network of cross-links in the resulting polymer. Linear and lightly crosslinked networks suffer from the disadvantage of having lower efficiency in raising the viscosity of a low molecular weight silicone. In addition to increasing the cost of the product, higher levels of crosslinked silicones result in leaving behind more residue when the volatile, low molecular weight silicone evaporates during use. In some cosmetic applications, e.g. deodorant or antiperspirants, an increased residue is a significant disadvantage as it contributes to staining of the clothing.

Further, linear and lightly crosslinked silicones do not form a film as easily as more tightly crosslinked silicones. The lack of a formation of a film is a disadvantage in a cosmetic application because a film provides a softer, smoother feel as compared to the heavier, less desirable feel of a linear silicone.

SUMMARY OF THE INVENTION

We now disclose that tightly cross-linked elastomers prepared from the addition polymerization of an alkenyl organopolysiloxane and an $M^HQ$ resin may be combined with a volatile low molecular weight silicone oil and processed to provide a desirable component for cosmetic compositions. The present invention provides for a silicone composition comprising:

(A) a silicone formed by the hydrosilylation product of (1) a linear alkenyl stopped polyorganosiloxane having the formula:

where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

where $R^1$ is a monovalent unsaturated hydrocarbon radical having from two to ten carbon atoms, and $R^2$ and $R^3$ are each independently one to forty carbon atom monovalent hydrocarbon radicals, with D defined as:

where $R^4$ and $R^5$ are each independently one to forty carbon atom monovalent hydrocarbon radicals, with $D^{vi}$ defined as:

$$D^{vi} = R^6 R^7 SiO_{2/2}$$

where $R^6$ is a monovalent unsaturated hydrocarbon radical having from two to ten carbon atoms, and $R^7$ is independently a one to forty carbon atom monovalent hydrocarbon radical with M defined as $$M = R^8 R^9 R^{10} SiO_{1/2}$$

with $R^8$, $R^9$, and $R^{10}$ each independently a one to forty carbon atom monovalent hydrocarbon radical; and (2) a resin having the formula:

$$(M^H{}_w Q_z)_j$$

where Q has the formula $SiO_{4/2}$ and with $M^H$ defined as $$H_b R^{11}{}_{3-b} SiO_{1/2}$$

where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a first silicone having a viscosity below about 1,000 centistokes at 25° C.;

thereby forming a gel having an ASTM D-2240-91 Durometer hardness of at least 5; and (B) a second silicone having a viscosity below about 1,000 centistokes at 25° C. wherein said gel is slurried in said second silicone and subjected to mixing with said second silicone;

producing thereby a uniform liquid comprising said second silicone and said gel whereby said uniform liquid has a viscosity ranging from 500 to 150,000 centistokes at 25° C.

The gel (having an ASTM D-2240-91 Durometer hardness of at least 5) is preferably prepared in a silicone selected from the group consisting of cyclic silicones having the formula:

$$D_f$$

where the subscript f is an integer ranging from about three to about 6 with D defined as:

$$R^4 R^5 SiO_{2/2}$$

where $R^4$ and $R^5$ are each independently one to forty carbon atom monovalent hydrocarbon radicals and linear silicones having the formula:

$$MD'_p M'$$

where D' is defined as:

$$R^4 R^5 SiO_{2/2}$$

where $R^4$ and $R^5$ are each independently one to forty carbon atom monovalent hydrocarbon radicals and M' has the formula:

$$R^{12} R^{13} R^{14} SiO_{1/2}$$

where $R^{12}$, $R^{13}$ and $R^{14}$ are each independently one to forty carbon atom monovalent hydrocarbon radicals.

The gel is preferably slurried and mixed in a silicone selected from the group consisting of cyclic silicones having the formula $$D_f$$

where the subscript f is an integer ranging from about three to about 6 with D defined as $$R^4 R^5 SiO_{2/2}$$

where $R^4$ and $R^5$ are each independently one to forty carbon atom monovalent hydrocarbon radicals and linear silicones having the formula $$MD'_p M'$$

where D' is defined as $$R^4 R^5 SiO_{2/2}$$

where $R^4$ and $R^5$ are each independently one to forty carbon atom monovalent hydrocarbon radicals and M' has the formula $$R^{12} R^{13} R^{14} SiO_{1/2}$$

where $R^{12}$, $R^{13}$ and $R^{14}$ are each independently one to forty carbon atom monovalent hydrocarbon radicals.

The present invention also provides a process for dispersing a silicone gel having an ASTM D-2240-91 Durometer hardness of at least 5 in a silicone liquid comprising:

(A) hydrosilylating (1) a linear alkenyl stopped polyorganosiloxane having the formula:

$$M^{vi}{}_a D_x D^{vi}{}_y M_{2-a}$$

where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

$$R^1 R^2 R^3 SiO_{1/2}$$

where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$$R^4 R^5 SiO_{2/2}$$

where $R^4$ and $R^5$ are each independently one to forty carbon atom monovalent hydrocarbon radicals, with $D^{vi}$ defined as:

$$D^{vi} = R^6 R^7 SiO_{2/2}$$

where $R^6$ is a monovalent unsaturated hydrocarbon radical having from two to ten carbon atoms, and $R^7$ is independently a one to forty carbon atom monovalent hydrocarbon radical with M defined as

with $R^8$, $R^9$, and $R^{10}$ each independently a one to forty carbon atom monovalent hydrocarbon radical; with (2) a resin having the formula:

where Q has the formula $SiO_{4/2}$ and with $M^H$ defined as

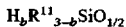

where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; in the presence of (3) a first silicone having a viscosity below about 1,000 centistokes at 25° C.; thereby (B) forming a gel having an ASTM D-2240-91 Durometer hardness of at least 5; and (C) slurrying said gel with a second silicone having a viscosity below about 1,000 centistokes at 25° C.; and (D) mixing said gel with said second silicone thereby (E) producing a uniform liquid comprising said second silicone and said gel whereby said uniform liquid has a viscosity ranging from 500 to 150,000 centistokes at 25° C.

DETAILED DESCRIPTION OF THE INVENTION

The composition of the present invention comprises the hydrosilylation addition product of (1) a linear alkenyl stopped polyorganosiloxane having the formula:

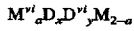

where the subscript x is a number greater than 500 preferably greater than 600, more preferably greater than 700, and most preferably greater than 800, the subscript y is a number ranging from zero to about 20, preferably ranging from zero to about 10, more preferably ranging from zero to about 5, and most preferably ranging from zero to about 4, the subscript a is a number ranging from 0 to 2, subject to the limitation that a+y is within the range of from 1 to about 20, preferably from one to about 10, more preferably from about 1.5 to about 10, and most preferably from about 1.5 to about 6, with $M^{vi}$ defined as:

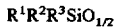

where $R^1$ is a monovalent unsaturated hydrocarbon radical having from two to ten carbon atoms, preferably styryl, allyl and vinyl, more preferably allyl and vinyl and most preferably vinyl and $R^2$ and $R^3$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl and mesityl; and most preferably from the group consisting of methyl and phenyl with D defined as:

where $R^4$ and $R^5$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl;

with $D^{vi}$ defined as:

$D^{vi}=R^6R^7SiO_{2/2}$ where $R^6$ is a monovalent unsaturated hydrocarbon radical having from two to ten carbon atoms, preferably styryl, allyl and vinyl, more preferably allyl and vinyl and most preferably vinyl and $R^7$ is independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and with M defined as $M=R^8R^9R^{10}SiO_{1/2}$ with $R^8$, $R^9$, and $R^{10}$ each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl and (2) a resin having the formula:

where Q has the formula $SiO_{4/2}$ and where $M^H$ has the formula $H_bR^{11}_{3-b}SiO_{1/2}$ with the subscript b ranging from 1 to 3, where $R^{11}$ is a one to forty carbon atom monovalent hydrocarbon radical, preferably a one to twenty carbon monovalent hydrocarbon radical, more preferably selected from the group consisting of methyl, ethyl, propyl, iso-propyl, n-butyl, iso-butyl, sec-butyl, tert-buty, pentyl, hexyl, heptyl, phenyl, benzyl, and mesityl; and most preferably selected from the group consisting of methyl and phenyl with the subscripts w and z having a ratio of 0.5 to 4.0 respectively, preferably 0.6 to 3.5, more preferably 0.75 to 3.0, and most preferably 1.0 to 3.0; and the subscript j ranging from about 2.0 to about 100, preferably from about 2.0 to about 30, more preferably from about 2.0 to about 10, and most preferably from about 3.0 to about 5.0; and (3) a silicone, wherein the mixture of (3) with the adduct of (1) and (2) has been subjected to shearing forces.

The hydrosilylation reaction is carried out in the presence of a hydrosilylation catalyst selected from the group of ruthenium, osmium, rhodium, iridium, palladium and platinum hydrosilylation catalysts. Exemplary of such catalysts are those described in U.S. Pat. Nos. 2,823,218; 3,159,601; 3,159,662; and 3,775,452.

Applicants define the silicone, component (3), as any organo-silicon compound having a viscosity below about 1,000 centistokes at 25° C., preferably below about 500 centistokes at °C., more preferably below about 250 centistokes at 25° C., and most preferably below 100 centistokes at 25° C. Thus low molecular weight cyclic silicones such as $D_3$, $D_4$, $D_5$, and $D_6$ (i.e. $D_f$ where the subscript f ranges from 3 to 6) where D is as previously defined with $R^4$ and $R^5$ preferably methyl as well as low molecular weight linear silicones having the formula $$M'D'_iM'$$

where the substituents on D' are independently selected from the same substituents as previously defined for D and M' has the formula $$R^{12}R^{13}R^{14}SiO_{1/2}$$

where $R^{12}$, $R^{13}$ and $R^{14}$ are each independently selected from the group of one to forty carbon atom monovalent hydrocarbon radicals, preferably one to twenty carbon monovalent hydrocarbon radicals, more preferably from the group consisting of methyl, ethyl, propyl, iso-propyl, n-butyl, iso-butyl, sec-butyl, tert-buty, pentyl, hexyl, heptyl, phenyl, benzyl, and mesityl; and most preferably from the group consisting of methyl and phenyl; and the subscript i ranges from 0 to about 300, preferably from 0 to about 100, more preferably from 0 to about 50, and most preferably from 0 to about 20 are such volatile, silicones. Preferably component (3) is a volatile low molecular weight silicone.

The materials used to prepare the gels of the present invention have been defined in terms of formulas that recite structural elements M, D, T and Q within the definitions commonly accepted in the practice of silicone chemistry. As individual molecules, or as pure compounds, the subscripts of these formulas can assume only integral values (including zero where appropriate). As complex mixtures of compounds, each of which individually satisfies the molecular definition, the subscripts in describing the mixture will assume non-integral values (including zero where appropriate). However, those non-integral values for a given subscript will still range between the upper limit and the lower limits of the range for that particular subscript when integral values are stipulated. Thus, for example in the pure compound description of component (1), the subscript a may have the values 0, 1 or 2. As a mixture of compounds, component (1) will have an average value for the subscript a that is dependent on the number of individual molecular species having a equal to 0, 1, and 2. The same explanation holds component (2).

Thus, the average subscripts for component (1), when component (1) is a vinyl functionalized silicone as the specific alkenyl functionalization and is a mixture of various vinyl containing compounds, as defined, will span a range of vinyl equivalent weights ranging from about 1,500 to about 150,000, preferably from about 4,500 to about 110,000, more preferably from about 10,000 to about 70,000, and most preferably from about 15,000 to about 45,000. It is to be noted that these equivalent weights are specific equivalent weights for vinyl substitution, substitution with other olefinic substituents would generate a different but comparable range of equivalent weights. Likewise, the average subscripts for component (2) as a mixture, as defined, will span a range of hydride equivalent weights ranging from about 80 to about 190, preferably from about 82 to about 170, more preferably from about 85 to about 150, and most preferably from about 87 to about 130.

Further it is desirable that the alkenyl functionality present in component (1) ranges on average of from about 1 to about 20 alkenyl groups per molecule, preferably from about 1 to about 10 alkenyl groups per molecule, more preferably from about 1.5 to about 10 alkenyl groups per molecule, and most preferably from about 1.5 to about 6 alkenyl groups per molecule. Additionally, it is desirable that the hydride functionality present in component (2) ranges on average of from about 8 to 400 SiH groups per molecule, preferably from about 8 to about 100 SiH groups per molecule, more preferably from about 8 to about 50 SiH groups per molecule, and most preferably from about 8 to about 20 SiH groups per molecule.

Components (1) and (2) (as pure compounds or mixtures) are catalytically reacted together in the presence of component (3) to produce a gel having a polymer content that is approximately from about 5 to about 75 weight percent crosslinked polymer, preferably from about 10 to about 60 weight percent crosslinked polymer, more preferably about 15 to about 40 weight percent crosslinked polymer, and most preferably about 20 to about 35 weight percent crosslinked polymer with the balance being the volatile, low molecular weight silicone oil. Once this initially produced gel is prepared, it is mixed with an additional quantity of a volatile, low molecular weight silicone, i.e. additional component (3) which is possibly different from the component (3) used to prepare the initially produced gel, and subjected to mixing or shearing forces to produce a uniform liquid gel that is from about 1 to about 25 weight percent crosslinked polymer, preferably from about 2 to about 20 weight percent crosslinked polymer, more preferably from about 3 to about 15 weight percent crosslinked polymer, and most preferably from about 3 to about 10 weight percent crosslinked polymer with the balance being the volatile, low molecular weight silicone oils, component (3) or a mixture of compounds satisfying the definition of component (3).

The gel initially produced is sufficiently viscous that liquid flow is not ordinarily observable. As a crosslinked polymeric material, the gel initially produced, having 25 weight percent crosslinked polymer network, has a Durometer hardness number, ASTM D-2240-91,of at least 5, preferably of at least 7, more preferably of at least 10 and most preferably of at least 15. ASTM test numbers for the Durometer hardness test are indicative of a material sufficiently resistant to flow that it may fairly be characterized as a solid.

The resistance to flow of the initially produced gel is overcome by high speed mixing or shearing wherein the resulting composition or mixture is a uniform liquid and has a viscosity ranging from about 500 to about 150,000 centistokes at 25° C., more preferably the resulting viscosity of the composition or mixture is from about 1,000 to about 100,000 centistokes at 25° C., and most preferably the resulting viscosity of the composition or mixture is from about 10,000 to about 60,000 centistokes at 25° C. By shearing, Applicants mean the imposition of a force upon the composition where the mixture is treated using a three roll mill, a two roll mill, a sand grinder, a colloid mill, a Gaulin homogenizer, a Sonilator, Ross™ mixer, Microfluidizer, etc.

Subjecting these compositions to a shearing force produces a component suitable for use in personal care or cosmetic applications that has an improved spreadability and an improved substance or feel. The personal care applications where this property is most desirable, including but not limited to, is in deodorants, antiperspirants, skin creams, facial creams, hair care products such as shampoos, mousses, styling gels, protective creams and color cosmetics such as lipsticks, foundations, blushes, makeup, and mascara; and other cosmetic formulations where silicone components have been added.

All United States patents referenced herein are herewith and hereby incorporated by reference.

EXPERIMENTAL

EXAMPLE 1

Preparation of Crosslinked Silicone Polymers in Volatile, Low Molecular Weight Silicone Oil The crosslinked silicone polymers were prepared by mixing a given silyl hydride species, a given vinyl species, and a volatile low molecular weight silicone oil in a reaction vessel and mixing. To such a mixture a standard hydrosilylation catalyst was added. Hydrosilylation in the presence of platinum catalysts is described in U.S. Pat. Nos. 3,159,601; 3,159,662; 3,220,972; 3,715,334; 3,775,452; and 3,814,730 herewith and hereby incorporated by reference. The mixture containing the hydrosilylation catalyst was heated and allowed to react at a given. Thus, for example, 1.11 grams of $(M^H_2Q)_4$, w=2, z=1, and j=4; 250 g of a vinyl terminated siloxane having an equivalent weight of 33.750 grams/ equivalent vinyl, and 650 g of octamethylcyclotetrasiloxane were added to a dough mixer and stirred. 100 g of 0.11% platinum catalyst in octamethylcyclotetrasiloxane was added. The reaction was stirred and heated to 80° C. for two hours. The reaction was cooled and the product was isolated. Following this general procedure compositions A through T were prepared. The vinyl siloxane was varied through these preparations:

1) divinyl siloxane (A) is $M^{Vi}D_xM^{Vi}$ where $M^{Vi}$ is $R^1R^2R^3SiO_{1/2}$ where $R^1$ is ($CH_2$=CH) and $R^2$ and $R^3$ are each independently $CH_3$, and D is $R^4R^5SiO_{2/2}$ where $R^4$ and $R^5$ are each independently $CH_3$, with x varied from approximately 450 to approximately 1250;

2) monovinyl siloxane (B) is $M^{Vi}D_yM$ where $M^{Vi}$ is $R^1R^2R^3SiO_{1/2}$ where $R^1$ is ($CH_2$=CH) and $R^2$ and $R^3$ are each independently $CH_3$, D is $R^4R^5SiO_{2/2}$ where $R^4$ and $R^5$ are each independently $CH_3$, with y approximately equal to 200 and M is $R^8R^9R^{10}SiO_{1/2}$ with $R^8$, $R^9$, and $R^{10}$ each independently $CH_3$; and 3) pentavinyl siloxane (C) is $MD_iD^{Vi}_kM$ where M is $R^8R^9R^{10}SiO_{1/2}$ with $R^8$, $R^9$, and $R^{10}$ each independently $CH_3$, D is $R^4R^5SiO_{2/2}$ where $R^4$ and $R^5$ are each independently $CH_3$, with i approximately equal to 200, and $D^{vi}$ defined as: $D^{vi}=R^6R^7SiO_{2/2}$ where $R^6$ is ($CH_2$=CH) and $R^7$ is independently $CH_3$, with k approximately equal to 5.

TABLE 1

Preparation of Crosslinked Polymeric Siloxane in Volatile, Low Molecular Weight Silicone Oil: $(M^H_2Q)_4$ Resin Reacted with Divinyl Terminated Siloxane (A)

| Comp'n | Si-H to Si-Vinyl Ratio | Divinyl Siloxane A, mol. wt. | Polymer, wt. % | Volatile, Low Mol. Wt. Silicone, wt. % | Platinum, ppm |
|---|---|---|---|---|---|
| A | 0.7/1.0 | 66800 | 25 | 75 | 10 |
| B | 0.9/1.0 | 66800 | 25 | 75 | 10 |
| C | 1.0/1.0 | 66800 | 25 | 75 | 10 |
| D | 1.1/1.0 | 66800 | 25 | 75 | 10 |
| E | 1.3/1.0 | 66800 | 25 | 75 | 10 |
| F | 1.5/1.0 | 66800 | 25 | 75 | 10 |
| G | 1.58/1.0 | 66800 | 25 | 75 | 10 |
| H | 1.3/1.0 | 33500 | 25 | 75 | 10 |
| I | 1.3/1.0 | 92700 | 25 | 75 | 10 |
| J | 1.3/1.0 | 66800 | 25 | 75* | 10 |
| U | 1.3/1.0 | 66800 | 50 | 50 | 5 |
| V | 1.3/1.0 | 66800 | 15 | 85 | 5 |

Note:
*With the exception of preparation J which utilized D5 (decamethylcyclopentasiloxane) all the other preparations utilized D4 (octamethylcyclotetrasiloxane).

Preparations A through G study variations in the hydride to vinyl ratio of the hydrosilylation reaction. Preparations E, H and I study variations in the molecular weight of the vinyl component of the hydrosilylation reaction. Preparations E and J study variations in the volatile, low molecular weight silicone oil.

The following preparations utilized a mixture of vinyl siloxane compounds, divinyl siloxane A and monovinyl siloxane B, in contrast to those preparations presented in Table 1 which utilized only one vinyl siloxane compound, divinyl siloxane A.

TABLE 2

Preparation of Crosslinked Polymeric Siloxane inn Volatile, Low Molecular Weight Silicone Oil: $(M^H_2Q)_4$ Resin Reacted with Mixed Divinyl Terminated Siloxane (A) and Monovinyl Siloxane (B)

| Comp'n | Si-H to Si-Vinyl Ratio | Divinyl Siloxane A, mol. wt. | Monovinyl Siloxane B, mol. wt. | A/B | Polymer, wt. % | Volatile, Low Mol. Wt. Silicone, wt. % | Platinum ppm |
|---|---|---|---|---|---|---|---|
| K | 1.3/1.0 | 66800 | 15900 | 90/10 | 25 | 75 | 10 |
| L | 1.3/1.0 | 66800 | 15900 | 80/20 | 25 | 75 | 10 |
| M | 1.3/1.0 | 66800 | 15900 | 70/30 | 25 | 75 | 10 |
| N | 1.3/1.0 | 66800 | 15900 | 60/40 | 25 | 75 | 10 |
| O | 1.3/1.0 | 66800 | 15900 | 50/50 | 25 | 75 | 10 |
| P | 1.1/1.0 | 66800 | 15900 | 90/10 | 25 | 75 | 10 |
| Q | 1.1/1.0 | 66800 | 15900 | 70/30 | 25 | 75 | 10 |
| R | 1.1/1.0 | 66800 | 15900 | 50/50 | 25 | 75 | 10 |

Preparations K through O vary the ratio of divinyl siloxane A to mon-vinyl siloxane B at a constant hydride to vinyl ratio. Preparations P through R again vary the ratio of divinyl siloxane A to mon-vinyl siloxane B but at a different constant hydride to vinyl ratio from that in K through O.

The following preparations utilized a mixture of vinyl siloxane compounds, divinyl siloxane A and pentavinyl siloxane C, in contrast to those preparations presented in Table 1 which utilized only one vinyl siloxane compound, divinyl siloxane A.

TABLE 3

Preparation of Crosslinked Polymeric Siloxane inn Volatile, Low Molecular Weight Silicone Oil: $(M^H_2Q)_4$ Resin Reacted with Mixed Divinyl Terminated Siloxane (A) and Pentavinyl Siloxane (C)

| Comp'n | Si-H to Si-Vinyl Ratio | Divinyl Siloxane A, mol. wt. | Pentavinyl Siloxane B, mol. wt. | A/B | Polymer, wt. % | Volatile, Low Mol. Wt. Silicone, wt. % | Platinum ppm |
|---|---|---|---|---|---|---|---|
| S | 1.3/1.0 | 66800 | 16200 | 90/10 | 25 | 75 | 10 |
| T | 1.3/1.0 | 66800 | 16200 | 80/20 | 25 | 75 | 10 |

The preparations reported in Table 3 vary the mixture of vinyl siloxanes being used to prepare the crosslinked material from that reported in Table 2.

EXAMPLE 2

Dilution of Crosslinked Gels with Volatile, Low Molecular Weight Silicone Oils

The crosslinked gels prepared in Example 1 were further diluted with volatile, low molecular weight silicone oils to produce a slurry. The volatile, low molecular weight silicone oils used for dilution were either the same as that used to prepare the crosslinked gel or different. The slurry was subjected to shearing forces in a homogenizer to produce a clear product of a desired viscosity for a specific cosmetic application. The viscosity of the gel volatile slurry that had been subjected to shearing forces ranged from about 100 centistokes to over about 100,000 centistokes at 25° C. Thus for example, 400 g of preparation E was blended with 1,600 g of D$_4$, octamethylcyclotetrasiloxane. Preparation E contains 25 wt. % crosslinked polymer, i.e. 100 g, and therefore the slurry of E in D$_4$ is 5 weight percent polymer. The mixture of 5 wt. % crosslinked polymer in D$_4$ was passed through a Gaulin homogenizer at 7,000 psi pressure. The resulting material was clear and had a viscosity of 120,000 centistokes at 25° C. The preparation of other material according to this general procedure is reported in Table 4.

TABLE 4

Viscosity of Sheared Crosslinked Silicone Polymers Diluted to 5 Wt. %

| Comp'n | Table 1 Gel | Wt. % Gel | Wt. % Volatile, Low Molecular Weight Silicone | Viscosity, cps at 25° C. |
|---|---|---|---|---|
| AA | A | 5 | 95 | 28,400 |
| BB | B | 5 | 95 | 35300 |
| CC | C | 5 | 95 | 61,800 |
| DD | D | 5 | 95 | 74,100 |
| EE | E | 5 | 95 | 115,000 |
| FF | F | 5 | 95 | 110,000 |
| GG | G | 5 | 95 | 112,000 |
| HH | H | 5 | 95 | 47,300 |
| II | I | 5 | 95 | 31,400 |
| JJ | J | 5 | 95 | 80,000 |
| KK | K | 5 | 95 | 72,700 |
| LL | L | 5 | 95 | 49,000 |
| MM | M | 5 | 95 | 27,200 |
| NN | N | 5 | 95 | 8,600 |
| OO | O | 5 | 95 | 2,500 |
| PP | P | 5 | 95 | 49,000 |
| QQ | Q | 5 | 95 | 22,000 |
| RR | R | 5 | 95 | 1,800 |
| SS | S | 5 | 95 | 81,700 |
| TT | T | 5 | 95 | 93,100 |
| UU | U | 6 | 94 | 20,000 |
| VV | V | 3.5 | 96.5 | 122,000 |

These data indicate that:
1) as hydride to alkenyl (vinyl) ratio is changed through 0.7 to 1.6 (hydride) to 1.0 (alkenyl) the product gel viscosity increases;
2) as the molecular weight of the alkenyl component increases, extending the distance between crosslink sites,
   i) the ability of the initially produced polymer gel to swell upon the addition of volatile silicones increases and
   ii) the viscosity increases; and
3) increasing the average functionality of the alkenyl precursor from 1.3 to 2.0, increases the crosslink density and the viscosity of the resulting product.

EXAMPLE 3

Comparison of Low Crosslink Density Gels with High Crosslink Density Gels

The processed gels of the present invention are gels that have a high crosslink density, due to the use of the M$^H$Q resin and vinyl siloxanes that a fairly low equivalent weight with respect to the vinyl group. For purposes of comparison, gels possessing a low density crosslinking network were prepared. Thus, the procedures outline to prepare the gels of example one were utilized with a linear hydride siloxane containing only two equivalents of hydride per molecule and a vinyl siloxane containing only two equivalents of vinyl per molecule (on average). Thus 2.02 g of a hydrogen terminated siloxane having a molecular weight of about 1,818 and 75 g of a vinyl terminated siloxane having a molecular weight of 67,500 were mixed with 425 g of octamethylcyclotetrasiloxane. The mixture was stirred and 10 ppm platinum catalyst was added as previously described. The mixture was heated to 80° C. for five hours. The product was cooled and isolated. The viscosity was 88.5 centistokes at 25° C. The results demonstrate that siloxane polymers made from low functionality ingredients produce siloxane polymers with little crosslinking and thus low efficiency in controlling the viscosity of the volatile siloxanes.

Having described the invention, that which is claimed is:
1. A silicone composition comprising:
(A) a silicone formed by the hydrosilylation product of
  (1) a linear alkenyl stopped polyorganosiloxane having the formula:

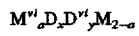

where the subscript x is a number greater than 500, the subscript y is a number ranging from zero to about 20, the subscript a is a number ranging from 0 to 2, subject to the limitation that a+y is within the range of from 1 to about 20, with M$^{vi}$ defined as:

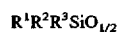

where R$^1$ is a monovalent unsaturated hydrocarbon radical having from two to ten carbon atoms, and R$^2$ and R$^3$ are each independently one to forty carbon atom monovalent hydrocarbon radicals, with D defined as:

where R$^4$ and R$^5$ are each independently one to forty carbon atom monovalent hydrocarbon radicals, with D$^{vi}$ defined as:

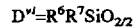

where R$^6$ is a monovalent unsaturated hydrocarbon radical having from two to ten carbon atoms, and R$^7$ is independently a one to forty carbon atom monovalent hydrocarbon radical with M defined as:

with R$^8$, R$^9$, and R$^{10}$ each independently a one to forty carbon atom monovalent hydrocarbon radical; and
(2) a resin having the formula:

where Q has the formula SiO$_{4/2}$ and with M$^H$ defined as:

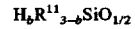

where R$^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a first silicone having a viscosity below about 1,000 centistokes at 25° C.;

thereby forming a gel having an ASTM D-2240-91 Durometer hardness of at least 5; and (B) a second silicone having a viscosity below about 1,000 centistokes at 25° C. wherein said gel is slurried in said second silicone and subjected to mixing with said second silicone;

producing thereby a uniform liquid comprising said second silicone and said gel whereby said uniform liquid has a viscosity ranging from 500 to 150,000 centistokes at 25° C.

2. The composition of claim 1 wherein in said linear alkenyl stopped polyorganosiloxane $R^1$ is a monovalent unsaturated hydrocarbon radical having two carbon atoms.

3. The composition of claim 2 wherein said linear alkenyl stopped polyorganosiloxane has a vinyl equivalent weight ranging from about 1,500 to about 150,000.

4. The composition of claim 3 wherein said resin has a hydride equivalent weight of from about 80 to about 190.

5. The composition of claim 4 wherein said first silicone is selected from the group consisting of cyclic silicones having the formula $$D_f$$

where the subscript f is an integer ranging from about three to about 6 with D defined as $$R^4R^5SiO_{2/2}$$

where $R^4$ and $R^5$ are each independently one to forty carbon atom monovalent hydrocarbon radicals and linear silicones having the formula:

$$M'D'_iM'$$

where D' is defined as:

$$R^4R^5SiO_{2/2}$$

where $R^4$ and $R^5$ are each independently one to forty carbon atom monovalent hydrocarbon radicals, the subscript i ranges from 0 to about 300, and M' has the formula:

$$R^{12}R^{13}R^{14}SiO_{1/2}$$

where $R^{12}$, $R^{13}$ and $R^{14}$ are each independently one to forty carbon atom monovalent hydrocarbon radicals.

6. The composition of claim 5 where said first silicone is a cyclic silicone.

7. The composition of claim 6 where f is 4.

8. The composition of claim 7 where said second silicone is selected from the group consisting of cyclic silicones having the formula $$D_f$$

where the subscript f is an integer ranging from about three to about 6 with D defined as:

$$R^4R^5SiO_{2/2}$$

where $R^4$ and $R^5$ are each independently one to forty carbon atom monovalent hydrocarbon radicals and linear silicones having the formula:

$$M'D'_iM'$$

where D' is defined as:

$$R^4R^5SiO_{2/2}$$

where $R^4$ and $R^5$ are each independently one to forty carbon atom monovalent hydrocarbon radicals and M' has the formula:

$$R^{12}R^{13}R^{14}SiO_{1/2}$$

where $R^{12}$, $R^{13}$ and $R^{14}$ are each independently one to forty carbon atom monovalent hydrocarbon radicals.

9. The composition of claim 8 where said second silicone is a cyclic silicone.

10. The composition of claim 9 where f is 4.

11. A process for dispersing a silicone gel having an ASTM D-2240-91 Durometer hardness of at least 5 in a silicone liquid comprising:

(A) hydrosilylating (1) a linear alkenyl stopped polyorganosiloxane having the formula:

$$M^{vi}_aD_xD^{vi}_yM_{2-a}$$

where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

$$R^1R^2R^3SiO_{1/2}$$

where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$$R^4R^5SiO_{2/2}$$

where $R^4$ and $R^5$ are each independently one to forty carbon atom monovalent hydrocarbon radicals, with $D^{vi}$ defined as:

$$D^{vi}=R^6R^7SiO_{2/2}$$

where $R^6$ is a monovalent unsaturated hydrocarbon radical having from two to ten carbon atoms, and $R^7$ is independently a one to forty carbon atom monovalent hydrocarbon radical with M defined as:

$$M=R^8R^9R^{10}SiO_{1/2}$$

with $R^8$, $R^9$, and $R^{10}$ each independently a one to forty carbon atom monovalent hydrocarbon radical; with (2) a resin having the formula:

$$(M^H_wQ_z)_j$$

where Q has the formula $SiO_{4/2}$ and with $M^H$ defined as:

$$H_bR^{11}{}_{3-b}SiO_{1/2}$$

where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; in the presence of
(3) a first silicone having a viscosity below about 1,000 centistokes at 25° C.; thereby
(B) forming a gel having an ASTM D-2240-91 Durometer hardness of at least 5; and
(C) slurrying said gel with a second silicone having a viscosity below about 1,000 centistokes at 25° C.; and
(D) mixing said gel with said second silicone thereby
(E) producing a uniform liquid comprising said second silicone and said gel whereby said uniform liquid has a viscosity ranging from 500 to 150,000 centistokes at 25° C.

12. The process of claim 11 wherein in said linear alkenyl stopped polyorganosiloxane $R^1$ is a monovalent unsaturated hydrocarbon radical having two carbon atoms.

13. The process of claim 12 wherein said linear alkenyl stopped polyorganosiloxane has a vinyl equivalent weight ranging from about 1,500 to about 150,000.

14. The process of claim 13 wherein said resin has a hydride equivalent weight of from about 80 to about 190.

15. The process of claim 14 wherein said first silicone is selected from the group consisting of cyclic silicones having the formula:

$$D_f$$

where the subscript f is an integer ranging from about three to about 6 with D defined as:

$$R^4R^5SiO_{2/2}$$

where $R^4$ and $R^5$ are each independently one to forty carbon atom monovalent hydrocarbon radicals and linear silicones having the formula:

$$M'D'_iM'$$

where D' is defined as $$R^4R^5SiO_{2/2}$$

where $R^4$ and $R^5$ are each independently one to forty carbon atom monovalent hydrocarbon radicals, the subscript i ranges from 0 to about 300, and M' has the formula:

$$R^{12}R^{13}R^{14}SiO_{1/2}$$

where $R^{12}$, $R^{13}$ and $R^{14}$ are each independently one to forty carbon atom monovalent hydrocarbon radicals.

16. The process of claim 15 where said first silicone is a cyclic silicone and f is 4.

17. The process of claim 16 where said second silicone is selected from the group consisting of cyclic silicones having the formula:

$$D_f$$

where the subscript f is an integer ranging from about three to about 6 with D defined as $$R^4R^5SiO_{2/2}$$

where $R^4$ and $R^5$ are each independently one to forty carbon atom monovalent hydrocarbon radicals and linear silicones having the formula:

$$M'D'_iM'$$

where D' is defined as:

$$R^4R^5SiO_{2/2}$$

where $R^4$ and $R^5$ are each independently one to forty carbon atom monovalent hydrocarbon radicals and M' has the formula:

$$R^{12}R^{13}R^{14}SiO_{1/2}$$

where $R^{12}$, $R^{13}$ and $R^{14}$ are each independently one to forty carbon atom monovalent hydrocarbon radicals.

18. The process of claim 17 where said second silicone is a cyclic silicone and f is 4.

19. A silicone composition consisting essentially of:
(A) a silicone formed by the hydrosilylation product of
(1) a linear alkenyl stopped polyorganosiloxane having the formula:

$$M''{}_aD_xD''{}_yM_{2-a}$$

where the subscript x is a number greater than 500, the subscript y is a number ranging from zero to about 20, the subscript a is a number ranging from 0 to 2, subject to the limitation that a+y is within the range of from 1 to about 20, with $M''{}^i$ defined as:

$$R^1R^2R^3SiO_{1/2}$$

where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$$R^4R^5SiO_{2/2}$$

where $R^4$ and $R^5$ are each independently one to forty carbon atom monovalent hydrocarbon radicals, with $D^{vi}$ defined as:

$$D''{}^i=R^6R^7SiO_{2/2}$$

where $R^6$ is a monovalent unsaturated hydrocarbon radical having from two to ten carbon atoms, and $R^7$ is independently a one to forty carbon atom monovalent hydrocarbon radical with M defined as:

$M = R^8R^9R^{10}SiO_{1/2}$ with $R^8$, $R^9$, and $R^{10}$ each independently a one to forty carbon atom monovalent hydrocarbon radical; and (2) a resin having the formula:

$(M^H{}_wQ_z)_j$ where Q has the formula $SiO_{4/2}$ and with $M^H$ defined as:

$H_bR^{11}{}_{3-b}SiO_{1/2}$ where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a first silicone having a viscosity below about 1,000 centistokes at 25° C.;

thereby forming a gel having an ASTM D-2240-91 Durometer hardness of at least 5; and (B) a second silicone having a viscosity below about 1,000 centistokes at 25° C. wherein said gel is slurried in said second silicone and subjected to mixing with said second silicone;

producing thereby a uniform liquid comprising said second silicone and said gel whereby said uniform liquid has a viscosity ranging from 500 to 150,000 centistokes at 25° C.

20. A process for dispersing a silicone gel having an ASTM D-2240-91 Durometer hardness of at least 5 in a silicone liquid consisting essentially of:

(A) hydrosilylating (1) a linear alkenyl stopped polyorganosiloxane having the formula:

$M^{vi}{}_aD_xD^{vi}{}_yM_{2-a}$ where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

$R^1R^2R^3SiO_{1/2}$ where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$R^4R^5SiO_{2/2}$ where $R^4$ and $R^5$ are each independently one to forty carbon atom monovalent hydrocarbon radicals, with $D^{vi}$ defined as:

$D^{vi} = R^6R^7SiO_{2/2}$ where $R^6$ is a monovalent unsaturated hydrocarbon radical having from two to ten carbon atoms, and $R^7$ is independently a one to forty carbon atom monovalent hydrocarbon radical with M defined as:

$M = R^8R^9R^{10}SiO_{1/2}$ with $R^8$, $R^9$, and $R^{10}$ each independently a one to forty carbon atom monovalent hydrocarbon radical; with (2) a resin having the formula:

$(M^H{}_wQ_z)_j$ where Q has the formula $SiO_{4/2}$ and with $M^H$ defined as:

$H_bR^{11}{}_{3-b}SiO_{1/2}$ where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; in the presence of (3) a first silicone having a viscosity below about 1,000 centistokes at 25° C.; thereby (B) forming a gel having an ASTM D-2240-91 Durometer hardness of at least 5; and (C) slurrying said gel with a second silicone having a viscosity below about 1,000 centistokes at 25° C.; and (D) mixing said gel with said second silicone thereby (E) producing a uniform liquid comprising said second silicone and said gel whereby said uniform liquid has a viscosity ranging from 500 to 150,000 centistokes at 25° C.

21. A cosmetic composition comprising a silicone composition comprising:

(A) a silicone formed by the hydrosilylation product of (1) a linear alkenyl stopped polyorganosiloxane having the formula:

$M^{vi}{}_aD_xD^{vi}{}_yM_{2-a}$ where the subscript x is a number greater than 500, the subscript y is a number ranging from zero to about 20, the subscript a is a number ranging from 0 to 2, subject to the limitation that a+y is within the range of from 1 to about 20, with $M^{vi}$ defined as:

$R^1R^2R^3SiO_{1/2}$ where $R^1$ is a monovalent unsaturated hydrocarbon radical having from two to ten carbon atoms, and $R^2$ and $R^3$ are each independently one to forty carbon atom monovalent hydrocarbon radicals, with D defined as:

$R^4R^5SiO_{2/2}$ where $R^4$ and $R^5$ are each independently one to forty carbon atom monovalent hydrocarbon radicals, with $D^{vi}$ defined as:

$D^{vi} = R^6R^7SiO_{2/2}$ where $R^6$ is a monovalent unsaturated hydrocarbon radical having from two to ten carbon atoms, and $R^7$ is independently a one to forty carbon atom monovalent hydrocarbon radical with M defined as:

$$M = R^8 R^9 R^{10} SiO_{1/2}$$

with $R^8$, $R^9$, and $R^{10}$ each independently a one to forty carbon atom monovalent hydrocarbon radical; and (2) a resin having the formula:

$$(M^H{}_w Q_z)_j$$

where Q has the formula $SiO_{4/2}$ and with $M^H$ defined as:

$$H_b R^{11}{}_{3-b} SiO_{1/2}$$

where $R^{11}$ is a one to forty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a first silicone having a viscosity below about 1,000 centistokes at 25° C.;

thereby forming a gel having an ASTM D-2240-91 Durometer hardness of at least 5; and (B) a second silicone having a viscosity below about 1,000 centistokes at 25° C. wherein said gel is slurried in said second silicone and subjected to mixing with said second silicone;

producing thereby a uniform liquid comprising said second silicone and said gel whereby said uniform liquid has a viscosity ranging from 500 to 150,000 centistokes at 25° C.

22. The composition of claim 21 wherein in said linear alkenyl stopped polyorganosiloxane $R^1$ is a monovalent unsaturated hydrocarbon radical having two carbon atoms.

23. The composition of claim 22 wherein said linear alkenyl stopped polyorganosiloxane has a vinyl equivalent weight ranging from about 1,500 to about 150,000.

24. The composition of claim 23 wherein said resin has a hydride equivalent weight of from about 80 to about 190.

25. The composition of claim 24 wherein said first silicone is selected from the group consisting of cyclic silicones having the formula $$D_f$$

where the subscript f is an integer ranging from about three to about 6 with D defined as $$R^4 R^5 SiO_{2/2}$$

where $R^4$ and $R^5$ are each independently one to forty carbon atom monovalent hydrocarbon radicals and linear silicones having the formula:

$$MD'_i M'$$

where D' is defined as:

$$R^4 R^5 SiO_{2/2}$$

where $R^4$ and $R^5$ are each independently one to forty carbon atom monovalent hydrocarbon radicals, the subscript i ranges from 0 to about 300, and M' has the formula:

$$R^{12} R^{13} R^{14} SiO_{1/2}$$

where $R^{12}$, $R^{13}$ and $R^{14}$ are each independently one to forty carbon atom monovalent hydrocarbon radicals.

26. The composition of claim 25 where said first silicone is a cyclic silicone.

27. The composition of claim 26 where f is 4.

28. The composition of claim 27 where said second silicone is selected from the group consisting of cyclic silicones having the formula $$D_f$$

where the subscript f is an integer ranging from about three to about 6 with D defined as:

$$R^4 R^5 SiO_{2/2}$$

where $R^4$ and $R^5$ are each independently one to forty carbon atom monovalent hydrocarbon radicals and linear silicones having the formula:

$$MD'_i M'$$

where D' is defined as:

$$R^4 R^5 SiO_{2/2}$$

where $R^4$ and $R^5$ are each independently one to forty carbon atom monovalent hydrocarbon radicals and M' has the formula:

$$R^{12} R^{13} R^{14} SiO_{1/2}$$

where $R^{12}$, $R^{13}$ and $R^{14}$ are each independently one to forty carbon atom monovalent hydrocarbon radicals.

29. The composition of claim 28 where said second silicone is a cyclic silicone.

30. The composition of claim 29 where f is 4.

* * * * *

UNITED STATES PATENT AND TRADEMARK OFFICE
CERTIFICATE OF CORRRECTION

PATENT NO. : 5,760,116
DATED : June 2, 1998
INVENTOR(S) : John A. Kilgour, et al.

It is certified that error appears in the above-identified patent and that said Letters Patent is hereby corrected as shown below:

On the title page, item [56], insert:

OTHER DOCUMENTS

| | | |
|---|---|---|
| | | WP 97/44010 Application - Wilson Lee et al. - COSMETIC CREAM COMPOSITION CONTAINING SILICONE GEL MATERIAL - 11/27/97 |
| | | |

Signed and Sealed this

Twenty-third Day of February, 1999

Q. TODD DICKINSON

*Attest:*

*Attesting Officer*   *Acting Commissioner of Patents and Trademarks*